United States Patent [19]

Regnier et al.

[11] Patent Number: 4,629,728
[45] Date of Patent: Dec. 16, 1986

[54] ANTIHYPOXEMIC 5-(4-SUBSTITUTED PIPERAZINYL)ALKYL-8-SUBSTITUTED QUINOLINES

[75] Inventors: Gilbert Regnier, Chatenay Malabry; Claude Guillonneau, Clamart; Jean Lepagnol, Chatou, all of France

[73] Assignee: ADIR S.A.R.L., Neuilly-sur-Seine, France

[21] Appl. No.: 686,247

[22] Filed: Dec. 26, 1984

[30] Foreign Application Priority Data

Jan. 4, 1984 [FR] France ............................... 84 00058

[51] Int. Cl.[4] ................... A61K 31/495; C07D 401/06
[52] U.S. Cl. ...................................... 514/252; 514/82;
544/243; 544/295; 544/337; 544/363
[58] Field of Search ............... 544/363, 337, 295, 243;
514/252, 82

[56] References Cited

U.S. PATENT DOCUMENTS 4,260,611 4/1981 Bartmann et al. ................... 544/363
4,514,401 4/1985 Tominaga et al. ................... 544/363

Primary Examiner—Richard L. Raymond
Assistant Examiner—James H. Turnipseed
Attorney, Agent, or Firm—Gordon W. Hueschen

[57] ABSTRACT

Quinoline compounds of the formula:

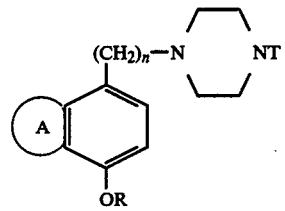

in which:

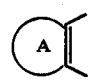

represents a group of the formula:

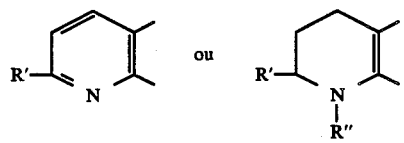

in which:
R' is hydrogen or methyl,
R and R" which are the same or different, each represents: hydrogen, ($C_1$–$C_5$) alkyl, ($C_1$–$C_5$) acyl haloacyl or aminoacyl, ($C_1$–$C_3$) alkylsulfonyl, or diethylphosphonyl;
n is an integer form 1 to 4 inclusive;
T is phenyl, halophenyl, trifluoromethylphenyl [($C_1$–$C_5$) alkyl] phenyl, [($C_1$–$C_5$) alkoxy] phenyl, or a five or six-membered heterocyclic radical containing one or two atoms selected from nitrogen and sulfur atoms optionally substituted by one or more ($C_1$–$C_5$) alkyl or ($C_1$–$C_5$) alkoxy.

These compounds and physiologically tolerable acid addition salts thereof may be used a medicines especially in the treatment of disorders connected with hypoxemia and energetic metabolic insufficiency especially during cerebral aging.

12 Claims, No Drawings

ANTIHYPOXEMIC 5-(4-SUBSTITUTED PIPERAZINYL)ALKYL-8-SUBSTITUTED QUINOLINES

The present invention provides quinoline compounds of the general formula I:

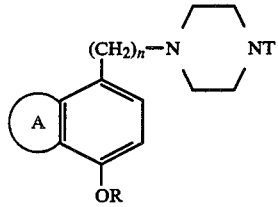

in which:

is selected from the group consisting of:

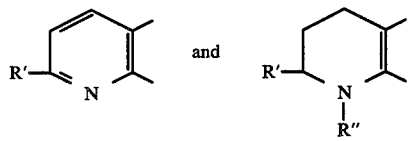

in which:
R' is selected from the group consisting of a hydrogen atom and a methyl radical;
R and R", which are the same or different, are each selected from the group consisting of:
a hydrogen atom,
$(C_1-C_5)$ alkyl radical,
$(C_1-C_5)$ acyl radicals, halo-$(C_1-C_5)$ acyl radicals and amino-$(C_1-C_5)$ acyl radicals,
$(C_1-C_3)$ alkylsulfonyl radicals, and
a diethylphosphonyl radical;
n is an integer selected from 1 to 4 inclusive, and
T is selected from the group consisting of:
a phenyl radical, (mono- and poly) halophenyl radicals trifluoromethylphenyl, hydrophenyl, [$(C_1-C_5)$alkyl]-phenyl and [$(C_1-C_5)$alkoxy]-phenyl radicals, and
five- and six-membered heterocyclic radicals having one or two atoms selected from nitrogen and sulfur atoms and these radicals substituted by a radical selected from the group consisting of $(C_1-C_5)$alkyl and $(C_1-C_5)$alkoxy radicals.

The present invention also provides a process for preparing a compound of the general formula I':

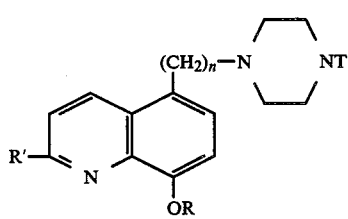

in which R, R', n and T are as above defined, which comprises condensing a halo compound of the general formula II:

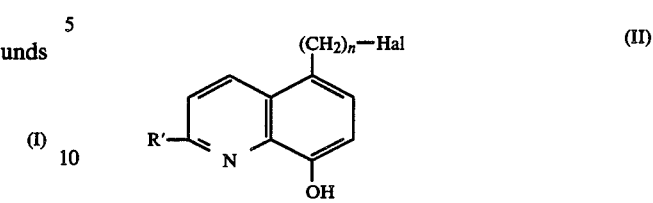

in which R' and n have the meanings above defined, and Hal represents a halogen atom such, for example, as a chlorine or a bromine atom, together with a N-monosubstituted piperazine of the general formula III:

in which T has the meaning previously given; then treating the so-obtained compound of the general formula IV:

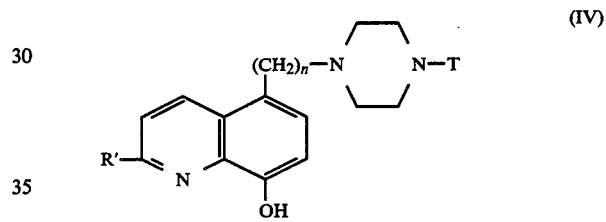

in which R', n and T have the meanings previously given, with a compound of the general formula V:

R—Z      (V)

in which R has the meaning previously defined and Z represents, according to the meanings of R, a halogen atom or one of the radicals: —$PO_3H$, COCl, $SO_2Cl$, or $ArSO_3$ in which Ar represents a phenyl group optionally substituted by one or more $(C_1-C_5)$alkyl radicals.

The condensation of compounds (II) and (III) may be carried out in a polar solvent such, for example, as an alcohol having from 1 to 4 carbon atoms, or dimethylformamide, at a temperature within the range of 60° to 120° C., in the presence of an acceptor of the hydrohalic acid formed during the reaction. As acceptors, there may be mentioned, for example, triethylamine, pyridine, alkali metal carbonates or an excess of the piperazine of the formula III.

For the transformation of compounds (IV) into compounds (I'), there may be used different reagents RZ, according to the meaning of R. For example, the diethylphosphates of the compounds (IV) may be prepared by phosphatation of the compounds (IV by the means of

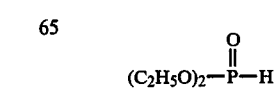

in an aprotic solvent (CCL4), at reflux, in the presence of triethylamine, according to a method described in J. Org. Chem. 42(2),345,(1977).

The esters of the compounds (IV) may be prepared according to a classic method, starting from the corresponding acid chlorides in pyridine or tetrahydrofuran in the presence of a tertiary base (triethylamine or pyridine) at a temperature within the range of 20° to 50° C.

The ethers of the compounds (IV) may be prepared according to classic methods such as alkylation of compounds IV (under alkali metal salt form) by the means of alkyl iodine or alkyl sulfonate, in a polar solvent, such, for example, as an alcohol at low boiling point, or dimethylformamide, at a temperature within the range of 60° to 90° C.

The present invention also provides a process for preparing the compounds of the general formula I":

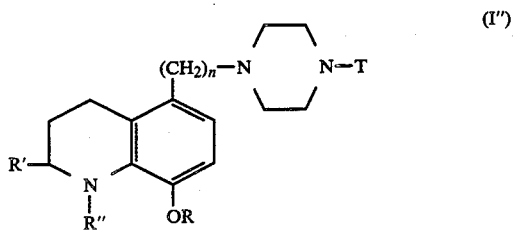

in which R, R', R", n and T have the meanings previously given, which comprises:

reducing the above prepared compound of the general formula I':

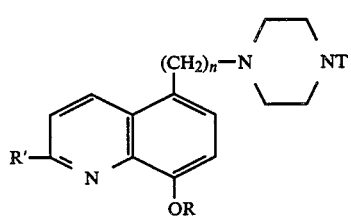

in which R, R', n and T are as above defined, into a compound of the general formula II':

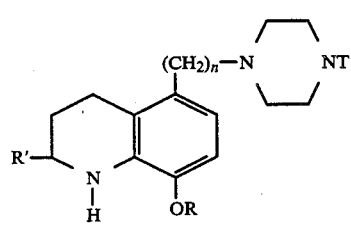

which is then treated with a reagent of the general formula III':

R"—Z    (III')

in which R" and Z are as above defined.

Compound I may be changed into compound II' by hydrogen reduction in the presence of a catalyst of the 8th group such as nickel or palladium on coal, in a polar solvent such as an alcohol with a low boiling point, under a pressure of $3 \times 10^6$ Pa to $11 \times 10^6$ Pa, at a temperature between 50° and 80° C.

The compounds of formula I", in which the meaning of R" is limited to an acyl radical, substituted or not, can be prepared according to a classic method similar to that described above in the process of preparation for the compounds of formula I', starting from an acyl halide in pyridine or in tetrahydrofuran, in the presence of triethylamine at a temperature between 20° and 60° C.

The compounds of formula I" in which the meaning of R" is limited to an alkyl radical, can be prepared, according to known methods, by alkylation of the compounds of formula II' using an iodide or an alkyl sulfonate in a polar solvent (alcohol, dimethylformamide) at a temperature between 10° and 25° C., in the presence of an acceptor of the formed hydrohalic acid (e.g. triethylamine), or by methods involving alkylating reduction (HCHO—HCOOH, or RCHO—H2/Pt or Pd/C, or NaBH3OOCR—RCOOH) or by reduction of the corresponding amides using AlLiH4. The group of compounds of general formulae I' and I" form the group of compounds of general formula I.

The raw materials of general formula II have been prepared according to the following operative diagram, starting from nitriles of formula (a), prepared according to the method of V. WARNER and al., J. Med. Chem. 19, 167-169, (1976).

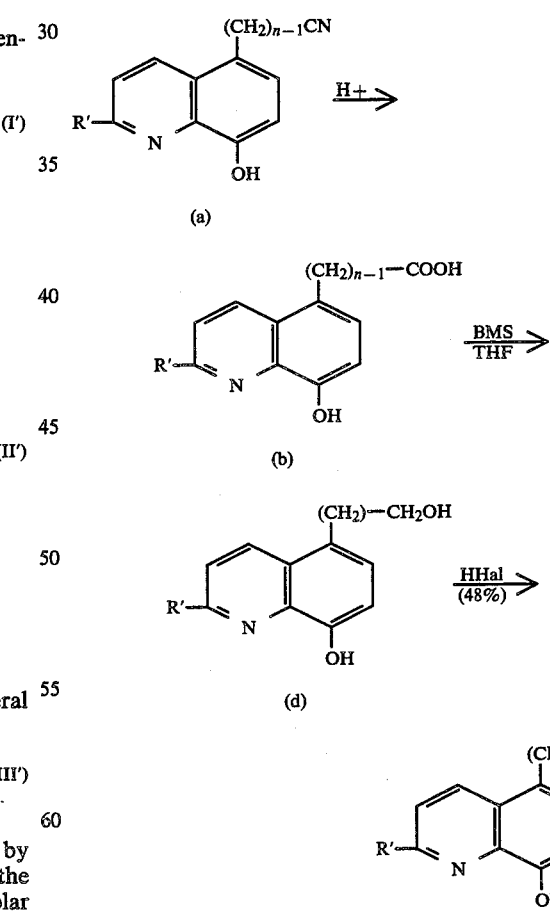

All the compounds can be regrouped under the general formula:

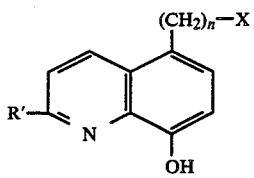

which has been exemplified in the following table:

| n | R' | x | Melting point (Kofler) |
|---|----|---|------------------------|
| 1 | H | Cl | 230° C. |
| 1 | H | CN | 174° C. |
| 1 | CH$_3$ | CN | 159° C. |
| 1 | H | COOH | 214° C. |
| 1 | CH$_3$ | COOH | 169° C. |
| 1 | H | CH$_2$OH | 95° C. |
| 1 | CH$_3$ | CH$_2$OH | Resinous product |
| 1 | H | CH$_2$Br | 116° C. |
| 1 | CH$_3$ | CH$_2$Br | Resinous product |
| 1 | H | CH$_2$Cl | 230° C. |
| 2 | H | COOH | 203° C. |
| 2 | H | CH$_2$OH | Resinous product |
| 2 | H | CH$_2$Br | Hydrobromide: 194–200° C. |

The starting N-monosubstituted piperazines (III) are known products.

The new compounds of general formula I can be transformed using acids into addition salts, salts which thus form part of the invention. As acids which may be used in the formation of these salts, there may be mentioned, for example, in the mineral series: hydrochloric, hydrobromic, sulfuric, and phosphoric acids and in the organic series: acetic, propionic, maleic, fumaric, tartaric, citric, oxalic, benzoic, methanosulfonic and isethionic acids.

The compounds of general formula I possess interesting pharmacological and therapeutic properties. They act against, on the one hand, pathological manifestations connected to the ischemic accident and, on the other hand, symptoms which accompany old age, in particular cerebral. These properties have a more intense effect than that of the antiischemic compounds used as reference whose activity has been recognised for a long time.

The compounds of general formula I are tested by their capacity to prolong the life of mice submitted to an acute global ischemic syndrome by intravenous injection of magnesium chloride. Thus when administered by intraperitoneal route, these compounds are capable of significantly prolonging the life of ischemied mice from a dose of 1 mg/kg as is the case for example, for the compounds of Examples 30, 38, 40 and 54 described hereinbelow.

Administered per os, they have similarly a protective effect, which is not the case of the reference substances in particular dihydroergotoxine which is inactive up to 10 mg/kg per os, and also vincamine and Ginkgo biloba extract which has no effect below 100 mg/kg per os.

In the same way, the compounds of general formula I show a protective effect in mice during an acute global hypoxic syndrome due to inhalation of pure azote. The beneficial action is seen at the same doses as for the previous test. The same effective dose relation is found with the reference substances.

The average effective dose (ED$_{50}$) increasing the survival time by 50% in relation to the control animals is approximately 3 mg/kg when these compounds are administered by intraperitoneal route or per os particularly with the compounds of Examples 38, 40, 51 and 54 described herein after.

On this test, the therapeutic index calculated by the relation LD$_{50}$/ED$_{50}$ is very favourable towards the compounds of general formula I since it is 30 times greater than that of the reference compounds vincamine, nicergoline, eburnamonine by intraperitoneal route and 5 times greater by oral route.

The protective activity vis-à-vis the losses of cortical electrogenesis connected to the ischemic or hypoxic syndrome is evaluated by the iterative anoxias test in rats. This test is modified in relation to its initial description in order to make it more severe and therefore more selective. After the second anoxia, whilst the control animals no longer recuperate their electrocortical activity, the animals treated with the compounds in particular the compounds described in Examples 30, 37, 38, 40 and 54 recover it when they have received by IV perfusion 33 micro g/kg of these. The reference substances only restore it later, at the 120th second for eburnamonine or nicergoline. Only dihydroergotoxine shows, when administered intravenously, a comparable activity.

The compounds of general formula I have been tested for their possible cerebral metabolic properties vis-à-vis an ischemic syndrome by hypoperfusion of 1 hour, thus of an extreme severity, or vis-à-vis an oedamatous impregnation generated by triethyl tin per os.

In both cases, the compounds show protective activities and stimulation of metabolic functions, as they prevent totally, or to a great extent, the appearance of oedema. For example, the compounds of Examples 30, 37, 51 and 54 hereinafter described, administered chronically for 4 days at 10 mg/kg, twice daily by intraperitoneal route, bring the percentage of water contained in the brain close to or to normal level. This protective activity is only as intense in the reference substances at higher doses, 5 times more for vincamine, 3 times more for nicergoline or extract of Ginkgo biloba, reputed to be powerful cerebral anti-oedema agents.

These same compounds show their pharmacological action vis-à-vis losses of the oxidative phosphorylation capacity of mitochondrias of the cerebral cortex obtained after an ischemic syndrome in rats. They restore the oxygen consumption of the mitochondria stimulated by ADP when the ischemied rat has received, by intraveous perfusion 0.1 mg/kg of compound I, in particular compounds of Examples 30, 38 and 54 described hereinafter. The same activity is only obtained for the reference products with dihydroergotoxine.

The compounds of general formula I may thus be used for oral or parenteral treatment in man in cases, of acute, transitory or progressive ischemic syndrome of any localisation as they have pharmacological properties vis-à-vis the many pathological manifestations which accompany the accidents. More generally, they are useful in the correction of disorders connected to hypoxemia and energetic metabolic insufficiency, for example during cerebral aging.

The present invention also relates to pharmaceutical compositions whose active principle is a compound of general formula I mixed or associated with a suitable pharmaceutical excipient. These compositions are presented in various forms such as tablets, dragees, capsules or preparations for sublingual, injectable or drinkable administrations.

The unit dosage may be from 1 to 30 mg to be taken once, twice or three times a day.

The following examples, given on a non-limitative basis, illustrate the invention. The melting points are determined, unless otherwise stated, using a Kofler hot plate.

EXAMPLE 1

5-2-4-(2-methoxyphenyl)-piperazinyl ethyl-8-hydroxy quinoline

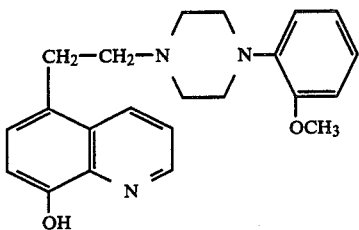

A mixture of 50.4 g of 5-bromoethyl-8-hydroxy quinoline, melting at 116° C., and 80.6 g of O.methoxyphenyl piperazine in 1 liter of ethanol is heated to reflux for 24 hours. At the end of this time, the crystals formed are suctioned off, washed with a little ethanol and the crystallised product is taken up with 600 ml of $Na_2CO_3$ at 10% by stirring for 3 hours. Then, the product is suctioned off, washed in water and vacuum-dried, and 63.5 g of 5-2-4-(2-methoxyphenyl)piperazinyl ethyl-8-hydroxy quinoline, are obtained in the form of beige crystals melting (capillary) at 170° C.

EXAMPLES 2 TO 20

The following compounds have been prepared according to the method described in Example 1:

2. 2-methyl-5-{2-[4-(2-methoxyphenyl)piperazinyl]ethyl}8-hydroxy quinoline, M.P.: 113° C. (cyclohexane).
3. 5-{2-[4-(1,3-thiazol-2-yl)piperazinyl]ethyl}-8-hydroxy quinoline, M.P.: 158° C. (ethanol/water).
4. 5-[4-(2-methoxyphenyl)piperazinyl methyl]-8-hydroxy quinoline, M.P. (capillary) of the corresponding dihydrochloride: 205°-215° C., with decomposition, (isopropanol).
5. 5-}3-[4-(2-methoxyphenyl)piperazinyl]propyl}-8-hydroxy quinoline, M.P. (capillary) of the corresponding dihydrochloride: 252°-254° C. (isopropanol/methanol).
6. 5-[2-(4-phenyl piperazinyl)ethyl]-8-hydroxy quinoline, M.P.: 186° C. (water).
7. 5-{2-[4-(2-pyridyl)piperazinyl]ethyl}-8-hydroxy quinoline, M.P.: 147° C. (water).
8. 5-{2-[4-(4-pyridyl)piperazinyl]ethyl}-8-hydroxy quinoline, M.P. (capillary) of the dihydrochloride: 246°-252° C. (methanol).
9. 5-{2-[4-(6-methoxy-2-pyridyl)piperazinyl]ethyl}-8-hydroxy quinoline, M.P.: 138° C. (isopropanol).
10. 5-{2-[4-(2-methylphenyl)piperazinyl]ethyl}-8-hydroxy quinoline, M.P.: 144° C. (n.propanol).
11. 5-{2-[4-(3-chlorophenyl)piperazinyl]ethyl}-8-hydroxy quinoline, M.P.: 136° C. (n.propanol).
12. 5-{2-[4-(3-trifluoromethylphenyl)piperazinyl]ethyl}-8-hydroxy quinoline, M.P.: 139° C. (n.propanol).
13. 5-{2-[4-(4-fluorophenyl)piperazinyl]ethyl}-8-hydroxy quinoline, M.P.: 170° C. (ethanol).
14. 5-{2-[4-(2-pyrimidinyl)piperazinyl]ethyl}-8-hydroxy quinoline, M.P.: 179° C. (water).
15. 5-{2-[4-(1,3,4-thiadiazol-2-yl)piperazinyl]ethyl}-8-hydroxy quinoline, M.P. (capillary): 183°-184° C. (water).
16. 5-{2-[4-(3-methyl-1,2,4-thiadiazol-5-yl)piperazinyl]ethyl}-8-hydroxy quinoline, M.P. (capillary): 204°-214° C. (isopropanol/water).
17. 5-{2-[4-(1,2,4-thiadiazol-5-yl)piperazinyl]ethyl}-8-hydroxy quinoline, M.P.: 190° C. (ethanol).
18. 5-{2-[4-(4-methoxyphenyl)piperazinyl]ethyl}-8-hydroxy quinoline, M.P.: 177° C. (water).
19. 5-{2-[4-(3-methoxyphenyl)piperazinyl]ethyl}-8-hydroxy quinoline, M.P.: 136° C. (water).
20. 5-{2-[4-(2-pyridyl)piperazinyl]ethyl}-8-hydroxy quinoline, M.P.: 136° C. (ethanol).

EXAMPLE 21

5-{2-[4-(2-methoxyphenyl)piperazinyl]ethyl}-8-methoxy quinoline

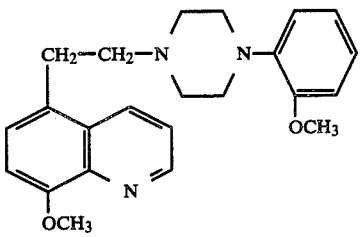

A solution of 56.4 g of 5-{2-[4-(2-methoxyphenyl)-piperazinyl]ethyl}-8-hydroxy quinoline, in 540 ml of anhydrous dimethylformamide with 3.72 g of sodium hydride is heated for 1 hour at 80° C., with 3.72 g of sodium hydride at 50% in oil.

Then, 30.3 g of p.toluene methyl sulfonate are added and the mixture heated for 3 hours at 90° C. At the end of this period, the dimethylformamide is evaporated off under reduced pressure and the residue is taken up with 500 ml of water and 500 ml of chloroform.

The chloroformic solution is washed several times with water and the chloroform is evaporated under reduced pressure. The oily residue weighing 58 g is purified by chromatoflash on 2.2 g of silica (230-240 mesh) by eluating with the mixture $CH_2Cl_2/CH_3OH$; 95/5).

46 g of 5-{2-[4-(2-methoxy phenyl)piperazinyl]ethyl}-8-methoxy quinoline were obtained, in the form of an oily product, whose fumarate melts (capillary) at 168° C. (ethanol).

EXAMPLES 22 TO 24

The following products have been prepared according to the method described in Example 21:

22. 5-{2-[4-(2-pyridyl)piperazinyl]ethyl}-8-methoxy quinoline, M.P. 94° C. (methylene chloride).
23. 1-methyl-5-{2-[4-(2-pyridyl)piperazinyl]ethyl}-8-methoxy-1,2,3,4-tetrahydro quinoline, M.P.: 116° C. (ethyl acetate).
24. 1-methyl-5-{2-[4-(2-methoxy phenyl)piperazinyl]ethyl}-8-methoxy-1,2,3,4-tetrahydro quinoline, M.P.: 94° C. (ethyl acetate).

Furthermore, using the same method as described in Example 21, but replacing the p.toluene methyl sulfonate by p.toluene ethyl sulfonate, the 8-ethoxy compounds are thus obtained.

EXAMPLE 25

5-{2-[4-(2-methoxyphenyl)piperazinyl]ethyl}-8-pivaloyloxy quinoline

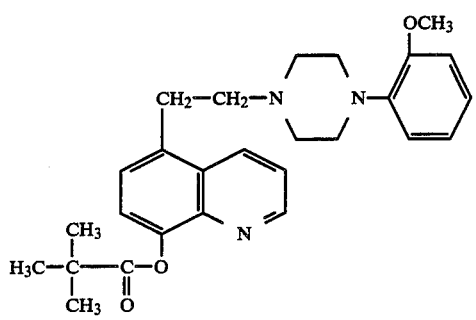

A mixture of 7.27 g of 5-{2-[4-(2-methoxyphenyl)piperazinyl]ethyl}-8-hydroxy quinoline in 150 ml of anhydrous tetrahydrofuran in the presence of 3.1 ml of triethylamine and 5 ml of pivaloyl chloride is stirred for 48 hours at room temperature. After evaporation of the tetrahydrofuran, the residue is taken up in chloroform and washed with a 10% NaHCO₃ solution. After evaporation of the chloroform, a crystalline residue is obtained which is recrystallised in 80 ml of isopropanol. Finally, 6.45 g of 5-{2-[4-(2-methoxyphenyl)piperazinyl]ethyl}-8-pivaloyloxy quinoline are obtained melting at 115° C.

The compound of the following Example has been prepared in the same way.

EXAMPLE 26

5-{2-[4-(2-methoxyphenyl)piperazinyl]ethyl}-8-methylsulfonyloxy quinoline, isolated in the form of a resin.

EXAMPLE 27

8-hydroxy diethylphosphate-5-{2-[4-(2-methoxyphenyl)piperazinyl]ethyl}quinoline

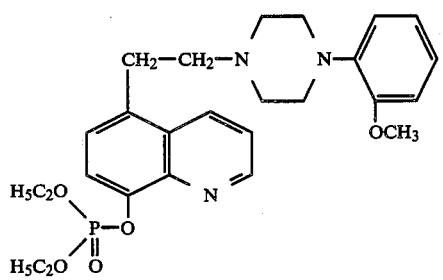

5.85 ml of freshly distilled diethylphosphate and 6.28 ml of triethylamine are added to a solution of 14.5 g of 5-{2-[4-(2-methoxyphenyl)piperazinyl]ethyl}-8-hydroxy quinoline in 320 ml of carbon tetrachloride at 55° C. After 22 hours at reflux, the insoluble substance is filtered off and the solvent is evaporated under reduced pressure. The residue is taken up in 200 ml of cyclohexane at reflux, the gummy insoluble substance is filtered and a crystallisation is observed on cooling. 18 g of 8-hydroxy diethylphosphate-5-{2-[4-(2-methoxyphenyl)piperazinyl]ethyl}quinoline are obtained, melting (capillary) at 88°–89° C. (cyclohexane).

According to the same method the compound of the following example has been prepared:

EXAMPLE 28

8-hydroxy diethylphosphate-5-{2-[4-(2-pyridyl)piperazinyl]ethyl}quinoline, M.P.: 70° C. (methylene chloride).

EXAMPLE 29

5-{2-[4-(2-methoxyphenyl)piperazinyl]ethyl}-8-hydroxy-1,2,3,4-tetrahydro quinoline

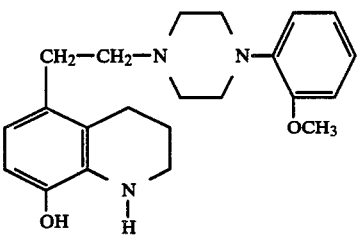

In an autoclave, a solution of 3.65 g of 5-{2-[4-(2-methoxyphenyl)piperazinyl]ethyl}-8-hydroxy quinoline, in 50 ml of ethanol, is hydrogenated for 20 hours at 85° C. under 125 atmospheres in the presence of Raney nickel. Then, it is filtered and concentrated to dryness under reduced pressure. The residue is dissolved in isopropanol and gaseous HCl is added to form the dihydrochloride. The crystals obtained (3.8 g) are then treated with a 10% Na₂CO₃ solution and the base is extracted in chloroform. After evaporation of the chloroform crystals of 5-{2-[4-(2-methoxyphenyl)piperazinyl]ethyl}-8-hydroxy-1,2,3,4-tetrahydro quinoline are obtained, melting (capillary) at 90° C.

EXAMPLE 30 TO 36

The following compounds have been prepared according to the method described in Example 29:

30. 5-{2-[4-(2-methoxyphenyl)piperazinyl]ethyl}-8-methylsulfonyloxy-1,2,3,4-tetrahydro quinoline, M.P. (capillary) of the corresponding fumarate: 184°–186° C. (ethanol).
31. 5-[2-(4-phenyl piperazinyl)ethyl]-8-hydroxy-1,2,3,4-tetrahydro quinoline, M.P.: 184° C. (isopropanol).
32. 5-{2-[4-(2-pyridyl)piperazinyl]ethyl}-8-hydroxy-1,2,3,4-tetrahydro quinoline, amorphous product.
33. 5-{2-[4-(2-methoxyphenyl)piperazinyl]ethyl}-8-methoxy-1,2,3,4-tetrahydro quinoline, M.P.: 88° C. (methylene chloride).
34. 5-{2-[4-(2-pyridyl)piperazinyl]ethyl}-8-methoxy-1,2,3,4-tetrahydro quinoline, M.P.: 109° C. (ethyl acetate).
35. 5-{2-[4-(3-trifluoromethyl phenyl)piperazinyl]ethyl}-8-methylsulfonyloxy-1,2,3,4-tetrahydro quinoline, M.P.: 132° C. (ethyl acetate).
36. 5-{2-[4-(2-methoxyphenyl)piperazinyl]ethyl}-8-phenylsulfonyloxy-1,2,3,4-tetrahydro quinoline, M.P. (capillary) of the corresponding dihydrochloride: 196°–200° C. (ethanol).

EXAMPLE 37

1-acetyl-5-{2-[4-(2-methoxyphenyl)piperazinyl]ethyl}-8-hydroxy-1,2,3,4-tetrahydro quinoline

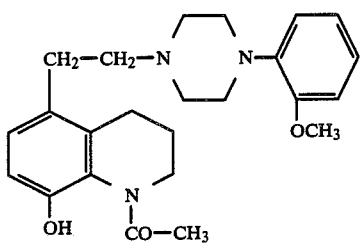

A solution of 1.45 ml of acetyl chloride is 20 ml of tetrahydrofuran is added at 5° C. to a solution of 7.34 g of 5-{2-[4-(2-methoxyphenyl)piperazinyl]ethyl}-8-hydroxy-1,2,3,4-tetrahydro quinoline in 140 ml of anhydrous tetrahydrofuran containing 2.8 ml of triethylamine. This is stirred for 2 hours at 5° C. and then for 1 hour at room temperature. Then, the insoluble substance is filtered off and concentrated to dryness under reduced pressure. The residue is purified by chromatoflash on 750 g of silica (70–230 mesh) by eluating with the mixture $CH_2Cl_3/CH_3OH$ (95/5).

5 g of 1-acetyl-5-{2-[4-(2-methoxyphenyl)-piperazinyl]ethyl}-8-hydroxy-1,2,3,4-tetrahydro quinoline hydrochloride are finally obtained melting (capillary) at 263°–265° C.

EXAMPLES 38 TO 50

The following compounds have been prepared according to the method described in Example 37:

38. 1-acetyl-5-{2-[4-(2-pyridyl)piperazinyl]ethyl}-8-hydroxy-1,2,3,4-tetrahydro quinoline, M.P.: 168° C. (ethyl acetate).
39. 1-acetyl-5-{2-[4-(2-pyridyl)piperazinyl]ethyl}-8-methoxy-1,2,3,4-tetrahydro quinoline, M.P.: 111° C. (ethyl acetate).
40. 1-acetyl-5-{2-[4-(2-methoxyphenyl)piperazinyl]ethyl}-8-methoxy-1,2,3,4-tetrahydro quinoline, M.P.: 112° C. (ethyl acetate).
41. 1-acetyl-5-{2-[4-(2-pyridyl)piperazinyl]ethyl}-8-acetoxy-1,2,3,4-tetrahydro quinoline, M.P.: 129° C. (methylene chloride).
42. 5-{2-[4-(2-methoxyphenyl)piperazinyl]ethyl}-8-dichloroacetyloxy-1,2,3,4-tetrahydro quinoline.
43. 5-{2-[4-(2-pyridyl)piperazinyl]ethyl}-8-dichloroacetoxy-1,2,3,4-tetrahydro quinoline.
44. 1-acetyl-5-{2-[4-(2-methoxyphenyl)piperazinyl]ethyl}-8-methylsulfonyloxy-1,2,3,4-tetrahydro quinoline, M.P. (capillary) of the corresponding dihydrochloride: 189°–197° C. (isopropanol).
45. 5-{2-[4-(2-methoxyphenyl)piperazinyl]ethyl}-8-methoxy-1,2,3,4-tetrahydro quinoline, amorphous product.
46. 1-acetyl-5-{2-[4-(2-pyridyl)piperazinyl]ethyl}-8-methylsulfonyloxy-1,2,3,4-tetrahydro quinoline, M.P. (capillary) of the corresponding dihydrochloride: 199°–201° C. (isopropanol/ether).
47. 1-propionyl-5-{2-[4-(2-pyridyl)piperazinyl]ethyl}-8-methylsulfonyloxy-1,2,3,4-tetrahydro quinoline, M.P. (capillary) of the corresponding dihydrochloride: 147°–154° C. (isopropanol/ether).
48. 1-acetyl-5-{2-[4-(3-trifluoromethylphenyl)-piperazinyl]ethyl}-8-methylsulfonyloxy-1,2,3,4-tetrahydro quinoline, M.P. (capillary) of the corresponding hydrochloride: 118°–123° C. (isopropanol/ether).
49. 1-acetyl-5-{2-[4-(2-methoxyphenyl)piperazinyl]ethyl}-8-acetoxy-1,2,3,4-tetrahydro quinoline, M.P. (capillary) of the corresponding dihydrochloride: 249°–252° C. (with decomposition) (isopropanol/ether).
50. 1-acetyl-5-{2-[4-(2-methoxyphenyl)piperazinyl]ethyl}-8-benzenesulfonyloxy-1,2,3,4-tetrahydro quinoline, M.P. (capillary) of the corresponding dihydrochloride: 165°–168° C. (ethanol).

EXAMPLE 51

1-methyl-5-{2-[4-(2-methoxyphenyl)piperazinyl]ethyl}-8-hydroxy-1,2,3,4-tetrahydro quinoline

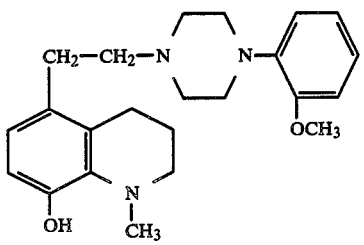

3.1 g of methyl iodide in 40 ml of absolute ethanol are added at 5° C. to a solution of 7.35 g of 5-{2-[4-(2-methoxyphenyl)piperazinyl]ethyl}-8-hydroxy-1,2,3,4-tetrahydro quinoline, in 80 ml of absolute ethanol. After 24 hours at room temperature, 0.5 g of methyl iodide are again added and stirring is maintained for 24 hours. Then the mixture is concentrated to dryness under reduced pressure and the residue is taken up in a 10% $NaHCO_3$ solution and chloroform. It is decanted and the chloroform evaporated to dryness. The residue is purified by chromatoflash on 700 g of silica by eluating with a mixture of $CH_2Cl_2/CH_3OH$ (95/5).

2.5 g of pure resinous product are obtained from which the dihydrochloride is formed in the isopropanol.

Finally, 2.3 g of white crystals are collected melting (capillary) at 168°–175° C.

In the same way, the compound of the following example has been prepared:

EXAMPLE 52

1-methyl-5-{2-[4-(2-pyridyl)piperazinyl]ethyl}-8-hydroxy-1,2,3,4-tetrahydro quinoline.

EXAMPLE 53

1-methyl-5-{2-[4-(2-methoxyphenyl)piperazinyl]ethyl}-8-methoxy-1,2,3,4-tetrahydro quinoline

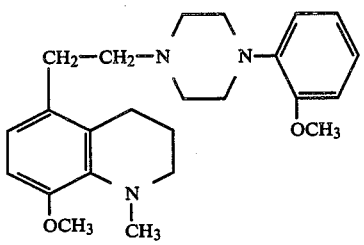

(a) First method

Proceeding as in Example 21, starting from 3 g of 1-methyl-5-{2-[4-(2-methoxyphenyl)piperazinyl]ethyl}-8-hydroxy-1,2,3,4-tetrahydro quinoline, 1.9 g of 1-methyl-5-}2-[4-(2-methoxyphenyl)piperazinyl]ethyl}-8-methoxy quinoline crystals are obtained melting (capillary) at 94° C.

Proceeding in the same manner, the 1-methyl-5-{2-[4-(2-pyridyl)piperazinyl]ethyl}-8-methoxy-1,2,3,4-tetrahydro quinoline already described in Example 23 was prepared.

(b) Second method

The 1-methyl-5-{2-[4-(2-methoxyphenyl)piperazinyl]ethyl}-8-methoxy-1,2,3,4-tetrahydro quinoline has also been prepared by reduction using LiAlH$_4$ in tetrahydrofuran on boiling the 1-formyl-5-{2-[4-(2-methoxyphenyl)piperazinyl]ethyl}-8-methoxy-1,2,3,4-tetrahydro quinoline, object of the following example.

EXAMPLE 54

1-formyl-5-{-2-[4-(2-methoxyphenyl)piperazinyl]ethyl}-8-methoxy-1,2,3,4-tetrahydro quinoline, M.P.: 110° C. (ethyl acetate). This compound has been prepared by formylation with 98% HCO OH on boiling of 5-{2-[4-(2-methoxyphenyl)piperazinyl]ethyl}-8-methoxy-1,2,3,4-tetrahydro quinoline, M.P.: 88° C.

EXAMPLE: 55-56

Proceeding in the same way as in Example 53 b), starting from 1-acetyl-5-{2-[4-(2-pyridyl)piperazinyl]ethyl}-8-methoxy-1,2,3,4-tetrahydro quinoline, and 1-acetyl-5-{2-[4-(2-methoxyphenyl)piperazinyl]ethyl}-8-methoxy-1,2,3,4-tetrahydro quinoline, the following compounds are respectively obtained:

55. 1-ethyl-5{2-[4-(2-pyridyl)piperazinyl]ethyl}-8-methoxy-1,2,3,4-tetrahydro quinoline.

56. 1-ethyl-5-{2-[4-(2-methoxyphenyl)piperazinyl]ethyl}-8-methoxy-1,2,3,4-tetrahydro quinoline.

We claim:

1. A compound selected from the group consisting of: quinoline compounds of the formula:

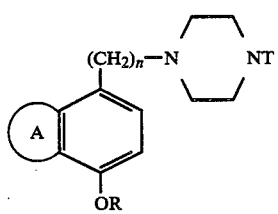

in which:

is selected from the group consisting of:

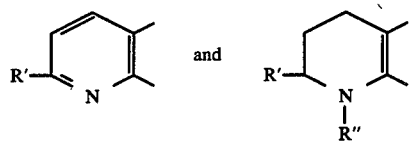

in which:

R' is selected from the group consisting of hydrogen and methyl;

R and R", which are the same or different, are each selected from the group consisting of:
hydrogen,
(C$_1$-C$_5$)alkyl,
(C$_1$-C$_5$)acyl, halo (C$_1$-C$_5$)acyl and amino-(C$_1$-C$_5$)acyl,
(C$_1$-C$_3$)alkylsulfonyl and
diethylphosphonyl;

n is an integer selected from 1 to 4 inclusive; and

T is selected from the group consisting of:
phenyl, halophenyl, trifluoromethylphenyl, hydroxyphenyl [(C$_1$-C$_5$)alkyl]-phenyl and [(C$_1$-C$_5$)alkoxy]-phenyl; and
five- and six-membered heterocyclic radicals having one or two atoms selected from nitrogen and sulfur and these radicals substituted by a radical selected from the groups consisting of (C$_1$-C$_5$)alkyl and (C$_1$-C$_5$)alkoxy; and physiologically tolerable acid addition salts thereof.

2. A compound of claim 1 which is 5-{2-[4-(2-methoxyphenyl)-piperazinyl]ethyl}-8-methoxy quinoline, and its fumarate.

3. A compound of claim 1 which is 5-{2-[4-(2-methoxyphenyl)-piperazinyl]ethyl}-8-methylsulfonyloxy-1,2,3,4-tetrahydroquinoline, and its fumarate.

4. A compound of claim 1 which is 5-{2-[4-(3-methoxyphenyl)-piperazinyl]ethyl}-8-hydroxy-1,2,3,4-tetrahydroquinoline, and its hydrochloride.

5. A compound of claim 1 which is: 1-acetyl-5-{2-[4-(2-pyridyl)-piperazinyl]ethyl}-8-hydroxy-1,2,3,4-tetrahydroquinoline.

6. A compound of claim 1 which is: 1-acetyl-5-{2-[4(2-pyridyl)piperazinyl]ethyl}-8-methoxy-1,2,3,4-tetrahydroquinoline.

7. A compound of claim 1 which is: 1-acetyl-5-{2-[4-(2-methoxyphenyl)-piperazinyl]ethyl}-8-methoxy-1,2,3,4-tetrahydroquinoline.

8. A compound of claim 1 which is: 1-methyl-5-{2-[4-(2-methoxyphenyl)-piperazinyl]ethyl}-8-hydroxy-1,2,3,4-tetrahydroquinoline, and its dihydrochloride.

9. A compound of claim 1 which is: 1-acetyl-5-{2-[4-(2-methoxyphenyl)-piperazinyl]ethyl}-8-methylsulfonyloxy-1,2,3,4-tetrahydroquinoline and its dihydrochloride.

10. A compound of claim 1 which is: 1-formyl-5-{2-[4-(2-methoxyphenyl)-piperazinyl]ethyl}-8-methoxy-1,2,3,4 tetrahydroquinoline.

11. Pharmaceutical compositions containing as active ingredient a compound of claim 1 together with a suitable pharmaceutical carrier.

12. A method for treating a living animal body afflicted with disorders connected with hypoxemia or energic metabolic insufficiency especially during cerebral aging, comprising the step of administering to the said living animal an amount of a compound of claim 1 which is effective for the alleviation of the said conditions.

* * * * *

UNITED STATES PATENT AND TRADEMARK OFFICE
CERTIFICATE OF CORRECTION

PATENT NO. : 4,629,728
DATED : December 16, 1986
INVENTOR(S) : Gilbert Regnier, Claud Guillonneau and Jean Lepagnol It is certified that error appears in the above-identified patent and that said Letters Patent is hereby corrected as shown below:

Col. 7, line 47; "5-}3-[4-" should read -- 5-{3-[4- --

Col. 11, line 16; "is" should read -- in --

Col. 14, line 43; "[4(2-pyridyl)piperazinyl]" should read -- [4-(2-pyridyl)-piperazinyl] --

Signed and Sealed this

Twelfth Day of January, 1988

Attest:

DONALD J. QUIGG

Attesting Officer

Commissioner of Patents and Trademarks